United States Patent
Fan et al.

(10) Patent No.: US 10,086,364 B2
(45) Date of Patent: Oct. 2, 2018

(54) METHODS OF CATALYTIC HYDROGENATION FOR ETHYLENE GLYCOL FORMATION

(71) Applicant: UNIVERSITY OF WYOMING, Laramie, WY (US)

(72) Inventors: Maohong Fan, Ames, IA (US); Tiberiu Popa, Laramie, WY (US)

(73) Assignee: UNIVERSITY OF WYOMING, Laramie, WY (US)

( * ) Notice: Subject to any disclaimer, the term of this patent is extended or adjusted under 35 U.S.C. 154(b) by 243 days.

(21) Appl. No.: 14/749,441

(22) Filed: Jun. 24, 2015

(65) Prior Publication Data
US 2015/0375209 A1  Dec. 31, 2015

Related U.S. Application Data

(60) Provisional application No. 62/017,696, filed on Jun. 26, 2014.

(51) Int. Cl.
 *C07C 29/149* (2006.01)
 *B01J 23/72* (2006.01)
 (Continued)

(52) U.S. Cl.
 CPC ........... *B01J 23/72* (2013.01); *B01J 19/0093* (2013.01); *B01J 37/035* (2013.01); *B01J 37/036* (2013.01); *C07C 29/149* (2013.01); *B01J 29/064* (2013.01); *B01J 29/14* (2013.01); *B01J 29/46* (2013.01); *B01J 35/023* (2013.01); *B01J 37/08* (2013.01);
 (Continued)

(58) Field of Classification Search
 CPC .................................................. C07C 29/149
 See application file for complete search history.

(56) References Cited

U.S. PATENT DOCUMENTS

3,518,206 A * 6/1970 Sowards et al.
4,112,245 A   9/1978 Zehner et al.
(Continued)

FOREIGN PATENT DOCUMENTS

EP   0060787 A1 *  9/1982

OTHER PUBLICATIONS

Lin, H. et al. "Cu/SiO2 hybrid catalysts containing HZSM-5 with enhanced activity and stability for selective hydrogenation of dimethyl oxalate to ethylene glycol", Applied Catalysis A: General 445-446 (2012) 287-296.*
(Continued)

*Primary Examiner* — Medhanit W Bahta
(74) *Attorney, Agent, or Firm* — Patterson + Sheridan, LLP (57) ABSTRACT

Embodiments described herein generally relate to hydrogenation catalysts, syntheses of hydrogenation catalysts, and apparatus and methods for hydrogenation. Methods for forming a hydrogenation catalyst may include mixing a silica generating precursor with a copper precursor and adding an ammonium salt to an end pH of between about 5 to about 9. Methods for hydrogenating an oxalate may include forming a reaction mixture by flowing a hydrogenation catalyst to a reactor, flowing a hydrogen source to the reactor, and flowing an oxalate to the reactor, wherein the hydrogenation catalyst has a particle size between about 10 nm to about 40 nm. Methods may further include reacting the oxalate to form ethylene glycol.

19 Claims, 3 Drawing Sheets

(51) Int. Cl.
*B01J 19/00* (2006.01)
*B01J 37/03* (2006.01)
*B01J 37/08* (2006.01)
*B01J 35/02* (2006.01)
*B01J 29/064* (2006.01)
*B01J 29/14* (2006.01)
*B01J 29/46* (2006.01)

(52) U.S. Cl.
CPC .. *B01J 2208/02* (2013.01); *B01J 2219/00792* (2013.01); *B01J 2219/00835* (2013.01); *B01J 2219/00873* (2013.01); *B01J 2219/00909* (2013.01); *B01J 2219/00916* (2013.01); *B01J 2219/00961* (2013.01); *B01J 2219/00963* (2013.01); *B01J 2219/00986* (2013.01); *B01J 2523/00* (2013.01); *Y02P 20/52* (2015.11)

(56) References Cited

U.S. PATENT DOCUMENTS

| | | |
|---|---|---|
| 4,453,026 A | 6/1984 | Tahara et al. |
| 4,496,781 A | 1/1985 | Jacobson et al. |
| 4,551,565 A | 11/1985 | Miyazaki et al. |
| 4,614,728 A | 9/1986 | Hirai et al. |
| 4,628,128 A | 12/1986 | Bartley |
| 4,628,129 A | 12/1986 | Bartley |
| 4,647,551 A | 3/1987 | Miyazaki et al. |
| 4,652,685 A | 3/1987 | Cawse et al. |
| 4,677,234 A | 6/1987 | Bartley |
| 5,345,005 A | 9/1994 | Thakur et al. |
| 2005/0121646 A1 | 6/2005 | Matsuoka et al. |

OTHER PUBLICATIONS

Al-Dughaither, A. S. et al. "HZSM-5 Zeolites with Different SiO2/Al2O3 Ratios. Characterization and NH3 Desorption Kinetics" Ind. Eng. Chem. Res. 2014, 53, 15303-15316.*

Zhang, Y. et al. "Effect of Copper Nanoparticles Dispersion on Catalytic Performance of Cu/SiO2 Catalyst for Hydrogenation of Dimethyl Oxalate to Ethylene Glycol", J. Nanomaterials, 2013, ID629375, pp. 1-6, Published Mar. 2013 (Year: 2013).*

Yin, A. et al. "Effect of Si/Al Ratio of Mesoporous Support on the Structure Evolution and Catalytic Performance of the Cu/Al-HMS Catalyst", J. Phys. Chem. C 2010, 114, 8523-8532 (Year: 2010).*

Zheng, Jianwei et al., "Efficient low-temperature selective hydrogenation of esters on bimetallic Au—Ag/SBA-15 catalyst", Elsevier, 2013, pp. 110-118.

Zhao, Tie-Jun et al., "Synthesis of Dimethyl Oxalate from CO and CH3ONO on Carbon Nanofiber Supported Palladium Catalysts", American Chemical Society, May 28, 2004, pp. 4595-4601.

Zhang, Xu et al., "Deactivation behavior of SiO2 supported copper catalyst in hydrogenation of diethyl oxalate", Journal of Fuel Chemistry and Technology, Sep. 2011, pp. 702-705.

Yue, Hairong et al., "Hydrogenation of Dimethyl Oxalate to Ethylene Glycol on a Cu/SiO2/Cordierite Monolithic Catalyst: Enhanced Internal Mass Transfer and Stability", American Institute of Chemical Engineers, pp. 2798-2809.

Yin, Anyuan et al., "Highly active and selective copper-containing HMS catalyst in the hydrogenation of dimethyl oxalate to ethylene glycol", Elsevier, 2008, pp. 91-99.

Yin, Anyuan et al., "Ag/MCM-41 as a highly efficient mesostructured catalyst for the chemoselective synthesis of methyl glycolate and ethylene glycol", Elsevier, 2011, pp. 90-99.

Xu, Gen-hui et al., "Kinetics of the Hydrogenation of Diethyl Oxalate to Ethylene Glycol", American Chemical Society, 1995, pp. 2371-2378.

Wen, Chao et al., "Remarkable Improvement of Catalytic Performance for a New Cobalt-Decorated Cu/HMS Catalyst in the Hydrogenation of Dimethyloxalate", Wiley-VCH Verlag GmbH& Co. KGaA, Weinheim, 2013, pp. 138-141.

Ward, John W., A Spectroscopic Study of the Surface of Zeolite Y. II. Infrared Spectra of Structural Hydroxyl Groups and Adsorbed Water on Alkali, Alkaline Earth, and Rare Earth Ion-Exchanged Zeolites, The Journal of Physical Chemistry—American Chemical Society, Nov. 1968, pp. 4211-4223.

Wang, Shengping et al., "Pd-Fe/a-Al2O3/cordierite monolithic catalysts for the synthesis of dimethyl oxalate: effects of calcination and structure", Higher Education Press and Springer-Verlag Berlin Heidelberg, 2012, pp. 259-269.

Wang, Shengping et al., "Characterization and catalytic activity of TiO2/SiO2 for transesterification of dimethyl oxalate with phenol", Elsevier, 2004, pp. 273-279.

Thomas, D. J. et al., "Hydrogenolysis of diethyl oxalate over copper-based catalysts", Elsevier Science Publishers B. V., Amsterdam, 1992, pp. 101-114.

Randall, D.J. et al., "Ammonia toxicity in fish", Elsevier, 2002, pp. 17-23.

Ma, Xinbin et al., "Hydrogenation of Dimethyl Oxalate to Ethylene Glycol over Mesoporous Cu-MCM-41 Catalysts", American Institute of Chemical Engineers, Jul. 2013, pp. 2530-2539.

Lin, Haiqiang et al., "Cu/SiO2 hybrid catalysts containing HZSM-5 with enhanced activity and stability for selective hydrogenation of dimethyl oxalate to ethylene glycol", Elsevier, 2012, pp. 287-296.

Li, Xinbao et al., "Ethylene Glycol and Ethanol Synthesis from Dimethyl Oxalate Hydrogenation on the Cu/ZnO/SiO2 catalysts", State Key Laboratory of Clean Energy Utilization, pp. 15-18.

Li, Zhenhua et al., "Effect of alkyl nitrite decomposition on catalytic performance of CO coupling reaction over supported palladium catalyst", Higher Education Press and Springer-Verlag Berlin Heidelberg, 2012, pp. 410-414.

Jacobs, Peter A. et al., "Evidence for the Nature of True Lewis Sites in Faujasite-Type Zeolites", American Chemical Society, 1979, pp. 1174-1177.

DeCanio Stephen J. et al., "Acid Catalysis by Dealuminated Zeolite-Y", Academic Press, Inc., 1986, pp. 132-141.

Ge, Yadong et al., "Influence of crystalline phase of Li—Al—O oxides on the activity of Wacker-type catalysts in dimethyl carbonate synthesis", Higher Education Press and Springer-Verlag Berlin Heidelberg, 2012, pp. 415-422.

Fernández, Maria B. et al., "Hydrogenation of sunflower oil over different palladium supported catalysts: Activity and selectivity", Elsevier, 2009, pp. 941-949.

* cited by examiner

METHODS OF CATALYTIC HYDROGENATION FOR ETHYLENE GLYCOL FORMATION

CROSS-REFERENCE TO RELATED APPLICATIONS

This application claims benefit of U.S. Provisional Patent Application No. 62/017,696, filed Jun. 24, 2014, which is incorporated herein by reference in its entirety.

FIELD

Embodiments described herein generally relate to hydrogenation catalysts, syntheses of hydrogenation catalysts, and apparatus and methods for hydrogenation.

BACKGROUND

Ethylene Glycol (EG) is a commodity used as antifreeze, in deicing products for aircraft and for the production of detergents, paints, cosmetics and polymers (such as polyesters). The process leading to the production of Ethylene Glycol from Dimethyl Oxalate (DMO) has been in development for more than a decade. Some of the advantages of synthesizing EG from DMO or Diethyl Oxalate (DEO) include: (a) the ability of using syngas generated by massive reserves of coal, thus reducing the demand for oil (which is the main raw material that produces an ethylene oxide intermediate), (b) a more profitable use of coal chemicals as compared to simple production of electricity for inferior and high moisture coal, (c) the capacity of stabilizing the price for EG as a commodity linked to the dimension of coal deposits, and (d) the capability of controlling $CO_2$ emitted through separation inside gasification installations, followed by other possible uses or storage/sequestration.

Furthermore, extensive reserves of low sulfur subbituminous coal exist in Wyoming, and these reserves are currently used for combustion in power plants despite having a water content that decreases the coal's heating value. The coal's water content has shifted interest toward using this valuable resource more efficiently and profitably. Gasification is one of the main techniques used as a more efficient use of coal. In particular, with gasification, water becomes a component of the reaction and the syngas produced can be used to produce higher value substances such as Dimethyl Oxalate and/or Diethyl Oxalate.

The use of a DMO/DEO hydrogenation reaction may include a $Cu/SiO_2$ catalyst, which may include one or more metallic additives. $Cu/SiO_2$ catalyst shows selectivity toward Ethylene Glycol (EG) and the stable Methyl Glycolate (MG) intermediate. Mesoporous materials (e.g., M41S group), hexagonal mesoporous silica (HMS), SBA-n, FSM-16, MCF, and MCM-41 have been reported as a silica ($SiO_2$) support. Furthermore, for increased internal mass transfer and stability and development for industrial implementation of the monolithic supports, $Cu/SiO_2$/cordierite may be used. However, the supports contain strong acid sites that will induce the intermolecular dehydration of ethylene glycol to ethanol, while the strong basic sites catalyze the formation of 1,2-butanediol.

Other supported metallic catalysts may include Ag/MCM-41 ($Ag/SiO_2$), Au—Ag/SBA-15. However, industrial applicability may be limited for these catalysts due to the price of certain metals.

The reaction of DMO (or DEO) to EG may occur in two steps, having a methyl glycolate (MG) intermediate:

$$CH_3OOCCOOCH_3 + 2H_2 \rightarrow CH_3OOCCH_2OH + CH_3OH$$
$$\Delta H_o = -30.03 \text{ kJ/mol} \quad (R1)$$

$$CH_3OOCCH_2OH + 2H_2 \rightarrow HOCH_2CH_2OH + CH_3OH$$
$$\Delta H_o = -28.70 \text{ kJ/mol} \quad (R2)$$

As mentioned above, the resultant EG can be further hydrogenated/dehydrated to ethanol, and other products might be generated like 1, 2-butanediol, ethane etc.

$$HO—CH_2—CH_2—OH + H_2 \rightarrow CH_3—CH_2—OH + H_2O$$
$$\Delta H_o = -87.20 \text{ kJ/mol} \quad (R3)$$

The hydrogenation reaction of DMO or DEO with a $Cu/SiO_2$ catalyst is generally operated at ~200° C., ~2 Mpa. It is considered that Cu as a catalyst allows the somewhat selective hydrogenation of C—O bonds without breaking C—C bonds. However, synthesis of $Cu/SiO_2$ catalysts by processes known in the art suffer from setbacks including:

poor stability of the metal-oxide interface and relatively fast sintering of copper aggregates, as well as over-reduction of surface cuprous species into $Cu^0$ during pretreatment and reaction;

relatively low catalytic activity and deactivation when operated at a high liquid hourly space velocity (LHSV) due to weak mechanical properties;

in order for porous catalyst sites to be accessible, DMO/DEO has to be able to enter through the pores of the catalyst, and pore size and particle size are difficult to predict and control;

most of the syntheses for this class of catalysts are slow and susceptible to generating materials of uneven activity. For example, current syntheses result in catalysts that either have selectivity for EG or efficient conversion of DMO/DEO, but not both selectivity and efficient conversion.

One method of $Cu/SiO_2$ catalyst formation is deposition-precipitation of copper using ammonia evaporation (AE) or urea decomposition (UD) on silica sol, sol-gel (SG) using Tetraethyl Orthosilicate (TEOS) or various pre-prepared siliceous based supports (MCM-41 SBA-15, ZSM5). Ammonia evaporation (AE) consists of adding ammonia to pH>10 for the formation of tetraamino cupric complexes followed by heating which eliminates ammonia by boiling (ammonia evaporation), which adjusts the pH to around 7 or less to promote precipitation of Cu compounds. In addition to the variation in copper deposition as a function of the rate of pH change and temperature during boiling associated with slow copper compound deposition, the ammonia evaporation method may be hazardous with risk of explosions, intoxications, and environmental damage upon scale up.

There is a need in the art for controlled methods of synthesizing hydrogenation catalysts that promote faster catalyst deposition and are safer and more environmentally favorable. There is also a need in the art for hydrogenation apparatus and catalysts, and methods of making such catalysts, that have high product selectivity and starting material conversion.

SUMMARY

Embodiments described herein generally relate to hydrogenation catalysts, syntheses of hydrogenation catalysts, and apparatus and methods for hydrogenation. In one embodiment, a method of forming a hydrogenation catalyst comprises mixing a silica generating precursor with a copper precursor for between about 1 minute and about 48 hours.

The method further comprises adding an ammonium salt to an end pH of between about 5 to about 9.

In another embodiment, a method of hydrogenating an oxalate comprises forming a reaction mixture by flowing a hydrogenation catalyst to a reactor, flowing a hydrogen source to the reactor, and flowing an oxalate to the reactor, wherein the hydrogenation catalyst has a particle size between about 10 nm to about 40 nm. The method further comprises reacting the oxalate to form ethylene glycol.

In another embodiment, an apparatus for hydrogenating an oxalate comprises a reactor configured to perform a hydrogenation process. The reactor is configured to contain a hydrogenation catalyst. The reactor is configured to contain a pressure between about 100 PSI to about 500 PSI and a temperature between about 150° C. to about 240° C. The apparatus further comprises a first gas source coupled with the reactor and configured to contain a hydrogen source. The apparatus further comprises a second gas source coupled with the reactor and configured to contain an oxalate and/or an oxalate precursor. The apparatus further comprises a controller configured to control the apparatus for performing the hydrogenation process.

BRIEF DESCRIPTION OF THE DRAWINGS

So that the manner in which the above recited features of the present disclosure can be understood in detail, a more particular description of the disclosure, briefly summarized above, may be had by reference to embodiments, some of which are illustrated in the appended drawings. It is to be noted, however, that the appended drawings illustrate only typical embodiments of this present disclosure and are therefore not to be considered limiting of its scope, for the present disclosure may admit to other equally effective embodiments.

To facilitate understanding, identical reference numerals have been used, where possible, to designate identical elements that are common to the figures. The figures are not drawn to scale and may be simplified for clarity. It is contemplated that elements and features of one embodiment may be beneficially incorporated in other embodiments without further recitation.

DETAILED DESCRIPTION

Embodiments described herein generally relate to apparatus and methods for hydrogenation, hydrogenation catalysts, and syntheses thereof. Apparatus generally comprise a reactor configured to perform a hydrogenation process, wherein the reactor is configured to contain a hydrogenation catalyst. Methods for forming a hydrogenation catalyst generally include mixing a silica generating precursor with a copper precursor and adding an ammonium salt to an end pH of between about 5 to about 9. Methods for hydrogenating an oxalate generally comprise forming a reaction mixture by flowing a hydrogenation catalyst to a reactor, flowing a hydrogen source to the reactor, and flowing an oxalate to the reactor, wherein the hydrogenation catalyst is synthesized using an ammonium salt, wherein the hydrogenation catalyst has a particle size between about 10 nm to about 40 nm.

Hydrogenation catalysts described herein may be prepared using any suitable reaction vessel, such as a round bottom flask or the like. Hydrogenation catalyst preparation may be carried out under inert conditions, such as an $N_2$ or Ar atmosphere. In some embodiments, hydrogenation catalysts, such as $Cu/SiO_2$, may be prepared by deposition-precipitation using one or more ammonium salts. An ammonium salt may include ammonium carbonate (($NH_4)_2CO_3$), ammonium acetate (($NH_4)OCOCH_3$), ammonium chloride ($NH_4Cl$), ammonium bicarbonate (($NH_4)OCOOH$), and mixtures thereof. In a reaction vessel, $Cu(NO_3)_2 \cdot xH_2O$ may be dissolved in water and stirred for between about 1 minute and about 48 hours, such as between about 5 minutes and about 24 hours, for example, about 30 minutes. A silicon generating precursor may be added to the $Cu(NO_3)_2 \cdot xH_2O$ solution and stirred for between about 1 minute and about 48 hours, such as between about 5 minutes and about 24 hours, for example, about 30 minutes. Silica generating precursors may include silica sol such as LUDOX® AS-30, colloidal silica such as AM-30, tetraethoxysilane (TEOS), zeolite such as ZSM-5 and Y-Zeolyst, or mixtures thereof. An ammonium salt may be added to the $Cu(NO_3)_2 \cdot xH_2O$/Silica generating precursor solution to achieve an end pH of the solution between about 3 to about 11, such as between about 5 to about 9, such as between about 6 to about 7. The ammonium salt may be added as a solid or as a solution, such as a saturated solution.

A precipitate, such as crystals, may form which may be filtered. The precipitate may be $Cu/SiO_2$ (about 20% Copper). The precipitate may be washed and/or dried at between about 70° C. to about 120° C., such as between about 80° C. to about 100° C., for example, about 89° C. The precipitate may be dried for between about 30 minutes to about 48 hours, such as between about 6 hours to about 24 hours, for example, about 12 hours. The precipitate may be calcined, for example, in air between about 200° C. to about 700° C., such as between about 300° C. to about 500° C., for example, about 450° C. The precipitate may be calcined for between about 30 minutes to about 48 hours, such as between about 2 hours to about 24 hours, for example, about 4 hours. The resulting material may also be crushed and sieved, the fractions of which may be, for example, between about 125 µm to about 250 µm. Ammonium salt deposition-precipitation provides for a controllable, single pH adjustment upon addition of the ammonium salt, in contrast with, for example, ammonia evaporation methods that require a less-controllable, double pH adjustment: first by addition of ammonia to increase the pH of the solution and second by boiling off ammonia to decrease the pH of the solution.

In some embodiments, catalysts may be prepared by deposition-precipitation using $NH_3$ as a precipitation agent. $Cu(NO_3)_2 \cdot xH_2O$ may be dissolved in water and stirred about 30 minutes. An ammonia solution (30%) may be added to the copper (II) nitrate aqueous solution to achieve a solution pH of between about 10 to about 11 and stirred about 30 minutes. Silica generating precursors may be added and stirred about 4 hours. The temperature may be raised to about 90° C. for evaporation of ammonia until about pH=7 to form a precipitate. The precipitate may be $Cu/SiO_2$ (about 20% Copper). The precipitate may be filtered, washed and dried at about 89° C. for about 12 hours. The resultant material may be calcined in air at about 450° C. for about 4 hours. The resultant material may be crushed and sieved, the fractions of which may be, for example, between about 125 µm and about 250 µm.

In some embodiments, catalysts may be prepared by sol-gel precipitation. $Cu(NO_3)_2 \cdot xH_2O$ may be dissolved in water and stirred about 30 minutes. An ammonia solution (30%) may be added to the copper (II) nitrate solution to achieve a solution pH of 10 to 11 and stirred about 30 minutes. A 1:1 mixture of TEOS and ethanol may be added to the copper solution and left for gelation. The TEOS/ethanol/copper solution may be boiled at about 70° C. to about pH=8 (for mass precipitation). The precipitate may be $Cu/SiO_2$ (about 20% Copper). The precipitate may be filtered and washed with water. The gel may be dried/aged in an oven at about 89° C. for about 12 hours. The resultant material may be calcined in air at about 450° C. for about 4 hours. The resultant material may be crushed and sieved, the fractions of which may be, for example, between about 125 µm and about 250 µm.

Figure 1:
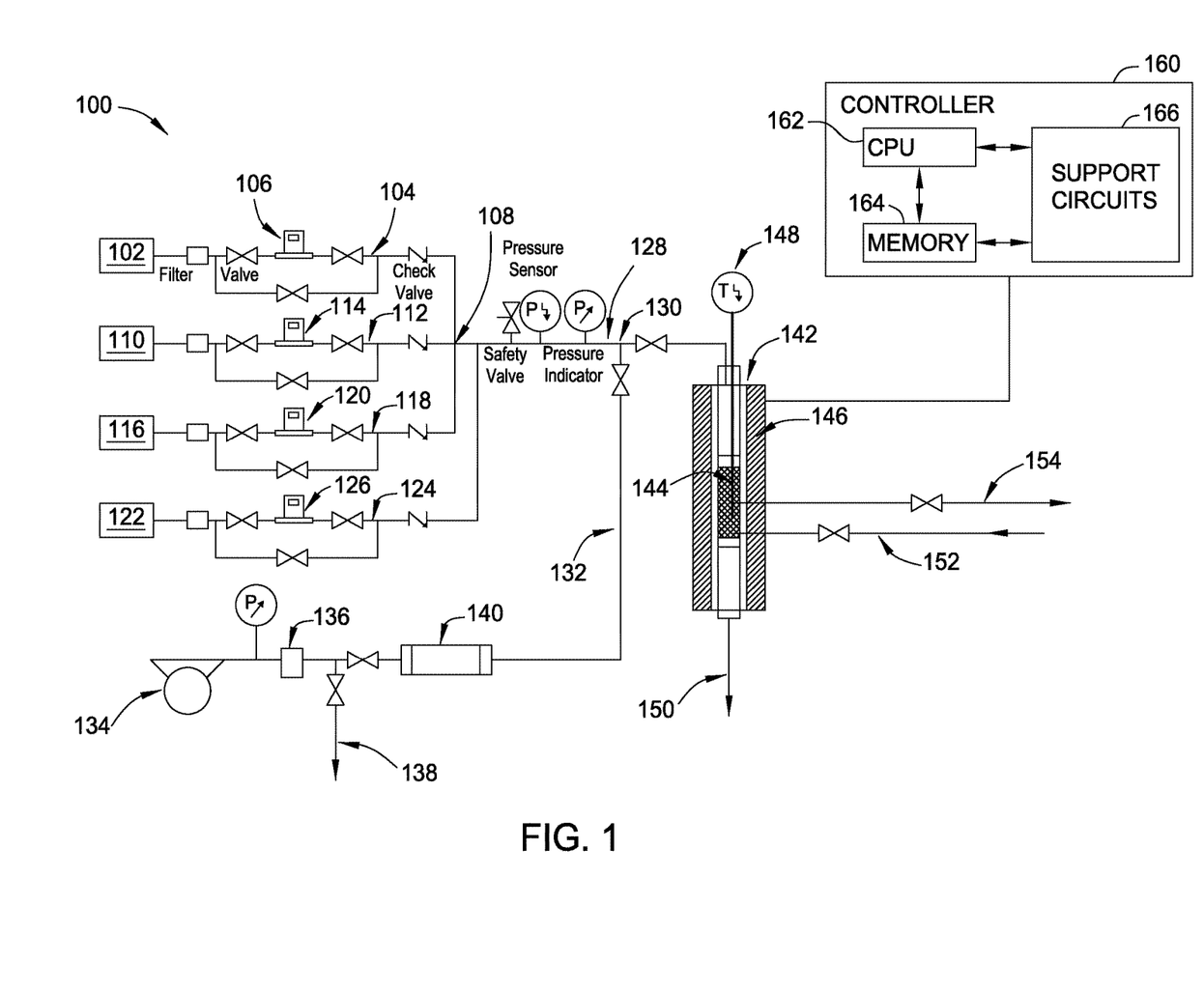
FIG. 1 is a schematic view of an apparatus 100 for performing hydrogenation, according to an embodiment.

FIG. 1 is a schematic view of an apparatus 100 for performing hydrogenation according to an embodiment of the present disclosure. Apparatus 100 includes a first gas source 102 for housing a first process gas, such as a hydrogen source, such as $H_2$. As described herein, "hydrogen source" is a chemical compound configured to deliver one or more hydrogen atoms to an oxalate during a hydrogenation process. A first flow channel 104 couples the first gas source 102 at a first end to a first mass flow controller 106 at a second end for fluid communication of first gas source 102 with first mass flow controller 106. The first mass flow controller 106 is configured to control the flow of the first process gas from the first gas source 102 to a mixing point 108 via first flow channel 104.

Apparatus 100 includes a second gas source 110 for housing a second process gas, such as a reaction gas, for example, CO, $CO_2$, DMO, DEO, or mixtures thereof. CO and/or $CO_2$ may be used to form DMO and DEO in-situ in a reactor 142 in the presence of methanol or ethanol, respectively. A second flow channel 112 couples the second gas source 110 at a first end to a second mass flow controller 114 at a second end for fluid communication of gas source 110 with second mass flow controller 114. The second mass flow controller 110 is configured to control the flow of the second process gas from the second gas source 110 to mixing point 108 via second flow channel 112.

Apparatus 100 includes a third gas source 116 for housing a third process gas, such as a carrier gas, such as $N_2$. A third flow channel 118 couples the third gas source 116 at a first end to a third mass flow controller 120 at a second end for fluid communication of third gas source 116 with third mass flow controller 120. The third mass flow controller 120 is configured to control the flow of the third process gas from the third gas source 116 to mixing point 108 via third flow channel 118.

Apparatus 100 includes a fourth gas source 122 for housing a fourth process gas, such as an internal gas standard, such as Ar or He. The fourth process gas may be used for calculating process gas conversion. A fourth flow channel 124 couples the fourth gas source 122 at a first end to a fourth mass flow controller 126 at a second end for fluid communication of fourth gas source 122 with fourth mass flow controller 126. The fourth mass flow controller 126 is configured to control the flow of the fourth process gas from the fourth gas source 122 to an intersection point along mixture flow channel 128 via fourth flow channel 124. Apparatus 100 includes a fifth flow channel 132. A vaporized liquid, such as methanol and/or ethanol, may be introduced to mixture flow channel 128 at a second mixing point 130 via fifth flow channel 132. Fifth flow channel 132 is coupled with mixture flow channel 128 at a first end and coupled with vaporizer 140 at a second end. The vaporization of the liquid may be accomplished via pump 134 in liquid communication with backpressure regulator 136 in liquid communication with drain 138 and vaporizer 140.

Apparatus 100 includes a reactor 142 comprising a catalytic bed 144 for housing one or more hydrogenation catalysts. The bottom and/or top portions of catalytic bed 144 may comprise inert material, such as ceramic wool. Catalyst introduction channel 152 is coupled with reactor 142 for introducing hydrogenation catalysts to catalytic bed 144. Catalyst removal channel 154 is coupled with reactor 142 for removing hydrogenation catalysts from catalytic bed 144. The reactor 142 further comprises a furnace 146 for regulating temperature within reactor 142. Thermocouple 148 is configured to detect the temperature within reactor 142. A first end of thermocouple 148 may be located on, in, or near catalytic bed 144. Reactor 142 may be controlled by, for example, a data acquisition (DAQ) system. Apparatus 100 comprises one or more filters, valves, check valves, safety valves, pressure sensors, and/or pressure indicators for further regulation of flow/introduction of the various gases and/or liquids of a particular hydrogenation process.

Apparatus 100 can be controlled by a processor based system controller such a controller 160. For example, the controller 160 may be configured to control apparatus 100 components and processing parameters associated with hydrogenation processes. The controller 160 includes a programmable central processing unit (CPU) 162 that is operable with a memory 164 and a mass storage device, an input control unit, and a display unit (not shown), such as power supplies, clocks, cache, input/output (I/O) circuits, and the like, coupled to the various components of the apparatus 100 to facilitate control of the hydrogenation process. The controller 160 also includes hardware for monitoring hydrogenation parameters through sensors in the apparatus 100, including sensors monitoring the various flow rates described herein, stirring rates (if used), temperatures, other reaction conditions, and sensors configured to receive feedback from and control said parameters.

To facilitate control of the apparatus 100 described above, the CPU 162 may be one of any form of general purpose computer processor that can be used in an industrial setting, such as a programmable logic controller (PLC), for controlling various chambers and sub-processors. The memory 164 is coupled to the CPU 162 and the memory 164 is non-transitory and may be one or more of readily available memory such as random access memory (RAM), read only memory (ROM), floppy disk drive, hard disk, or any other form of digital storage, local or remote. Support circuits 166 are coupled to the CPU 162 for supporting the processor in a conventional manner. Information obtained from hydrogenation with apparatus 100, GC, GC-MS and other processes are generally stored in the memory 164, typically as a software routine. The software routine may also be stored and/or executed by a second CPU (not shown) that is remotely located from the hardware being controlled by the CPU 162.

The memory 164 is in the form of computer-readable storage media that contains instructions, that when executed by the CPU 162, facilitates the operation of the apparatus 100. The instructions in the memory 164 are in the form of a program product such as a program that implements the method of the present disclosure. The program code may conform to any one of a number of different programming languages. In one example, the disclosure may be implemented as a program product stored on computer-readable storage media for use with a computer system. The program(s) of the program product define functions of the embodiments (including the methods described herein). Illustrative computer-readable storage media include, but are not limited to: (i) non-writable storage media (e.g., read-only memory devices within a computer such as CD-ROM disks readable by a CD-ROM drive, flash memory, ROM chips or any type of solid-state non-volatile semiconductor memory) on which information is permanently stored; and (ii) writable storage media (e.g., floppy disks within a diskette drive or hard-disk drive or any type of solid-state random-access semiconductor memory) on which alterable information is stored. Such computer-readable storage media, when carrying computer-readable instructions that direct the functions of the methods and apparatus described herein, are embodiments of the present disclosure.

A hydrogenation process, for example, within reactor 142 of apparatus 100 may be performed at a pressure between about 100 PSI (pounds per square inch) to about 500 PSI, such as between about 200 PSI to about 400 PSI, for example, about 300 PSI. A hydrogenation process, for example, within reactor 142 of apparatus 100 may be performed at a temperature between about 100° C. to about 300° C., such as between about 150° C. to about 240° C., such as between about 170° C. to about 220° C. Hydrogenation products, such as EG, and unreacted starting material may be flowed from reactor 142 to a storage tank (not shown) via sixth flow channel 150. Hydrogenation products and unreacted starting material, such as DMO and/or DEO, may be flowed to a gas chromatograph (GC) or gas chromatograph-mass spectrometer (GC-MS) for analysis of the hydrogenation products, conversion, etc. In some embodiments, a hydrogenation process is performed in a reactor, such as reactor 142, and the process performed within the reactor comprises a reaction mixture containing a hydrogen source, such as $H_2$, between about 50 v % (volume %) to about 99.9 v %, about 80 v % to about 95 v %, about 92 v %. In some embodiments, the reaction mixture contains a carrier gas, such as $N_2$, between about 0.1% to about 70%, about 1% to about 15%, about 7%. In some embodiments, the reaction mixture contains a ratio of hydrogen source to reactant, such as DMO and/or DEO, between about 100:1 (hydrogen source: DMO/DEO) to about 0.1:1, about 90:1 to about 50:1, about 80:1. In some embodiments, a hydrogenation process is performed with DMO and/or DEO about 10% by weight in methanol and/or ethanol.

In some embodiments, a hydrogenation process is performed with a hydrogenation catalyst, such as $Cu/SiO_2$, that may be diluted with quartz sand for further temperature control of the hydrogenation process. In some embodiments, a hydrogenation catalyst contains copper, such as $Cu/SiO_2$, and the ratio of copper in the catalyst to DMO and/or DEO is between about 0.1:1 (Cu:DMO/DEO) to about 100:1, about 0.1:1 to about 10:1, about 0.3:1 to about 1:1. As described herein, a weight hourly space velocity may be determined by grams of reactant, such as DMO/DEO, divided by grams of catalyst. In some embodiments, a weight hourly space velocity (WHSV) is between about 0.1 and about 100, about 0.3 and about 10, about 0.8 and about 2, about 0.8. In some embodiments, before DMO and/or DEO are introduced into a reactor, such as reactor 142, a reduction reaction of a hydrogenation catalyst, such as $Cu/SiO_2$, is carried out in an atmosphere containing a hydrogen source, such as $H_2$, and a carrier gas, such as $N_2$.

The reduction reaction may be carried out at between about 300° C. to about 400° C., such as between about 350° C. The reduction reaction may be carried out for between about 30 minutes to about 10 hours, such as between about 2 hours to about 6 hours, for example about 4 hours.

The temperature of the reactor may then be maintained, reduced or increased, followed by introduction of CO, $CO_2$, DMO and/or DEO into the reactor. Alternatively, a hydrogenation catalyst may be introduced into a reactor containing DMO and/or DEO. In some embodiments, zeolites may be used in addition to silica or as an alternative to silica. The zeolites may comprise $SiO_2/Al_2O_3$ ratios between about 0.1:100 and about 100:0.1, between about 1:50 and about 50:1, about 1:10 and about 10:1, about 1:1. In some embodiments, a $SiO_2/Al_2O_3$ ratio is about 80:1. Zeolites are configured to capture cations in their cavities, thus stabilizing Cu+[1] and other metals. Zeolites also possess large variability in terms of $SiO_2/Al_2O_3$ ratio, number of acid sites, strength of their acid sites, etc. Zeolites also possess large surface areas and may be economically utilized in industrial production since they are widely used in refineries for cracking/hydrocracking operations.

Figure 2:
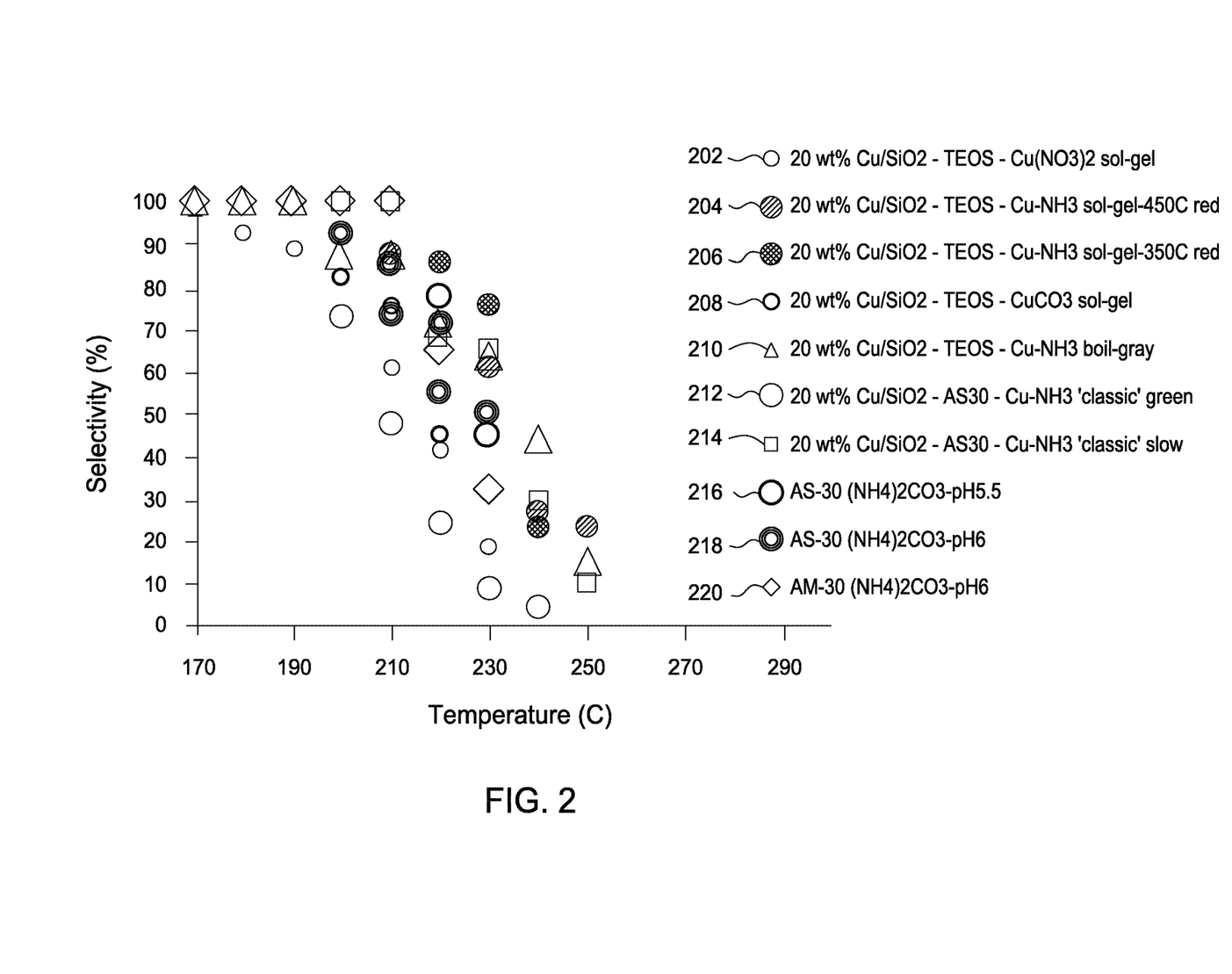
FIG. 2 illustrates the selectivity of DMO to form EG and MG using various catalysts, according to an embodiment.

FIG. 2 illustrates the selectivity of DMO to form EG and Methyl Glycolate Intermediate (MG) using various catalysts, according to some embodiments of the present disclosure. Hydrogenation conditions: catalyst mass corresponding to 0.3 g Cu (about 1.5 g of catalyst), 300 PSI pressure, temperature at least 170° C., weight hourly space velocity (WHSV) 0.8 (g DMO h/g cat), initial gaseous phase 92.6% v. % $H_2$, 7.4 v % $N_2$, $H_2$/DMO mol ratio 80:1, initial liquid phase 10 wt % DMO/methanol. As shown in FIG. 2, catalysts 204-220 result in selectivity, i.e. products containing C—C bonds: only EG and MG, until 200° C. (as shown by the overlapping data points of 204-220). Catalysts produced using ammonia-based processes (described above) (catalysts 204, 206, 210 and 212) decrease in selectivity above 190° C. (Note: the 204 data point overlaps with the 218 data point at 200° C.). Catalysts prepared from ammonium carbonate (208, 216, 218 and 220) showed selectivity similar to the catalysts prepared using ammonia fast gelation (described above) (Note: 210 and 212) (the 216 data point overlaps with the 220 data point at 230° C.).

Figure 3:
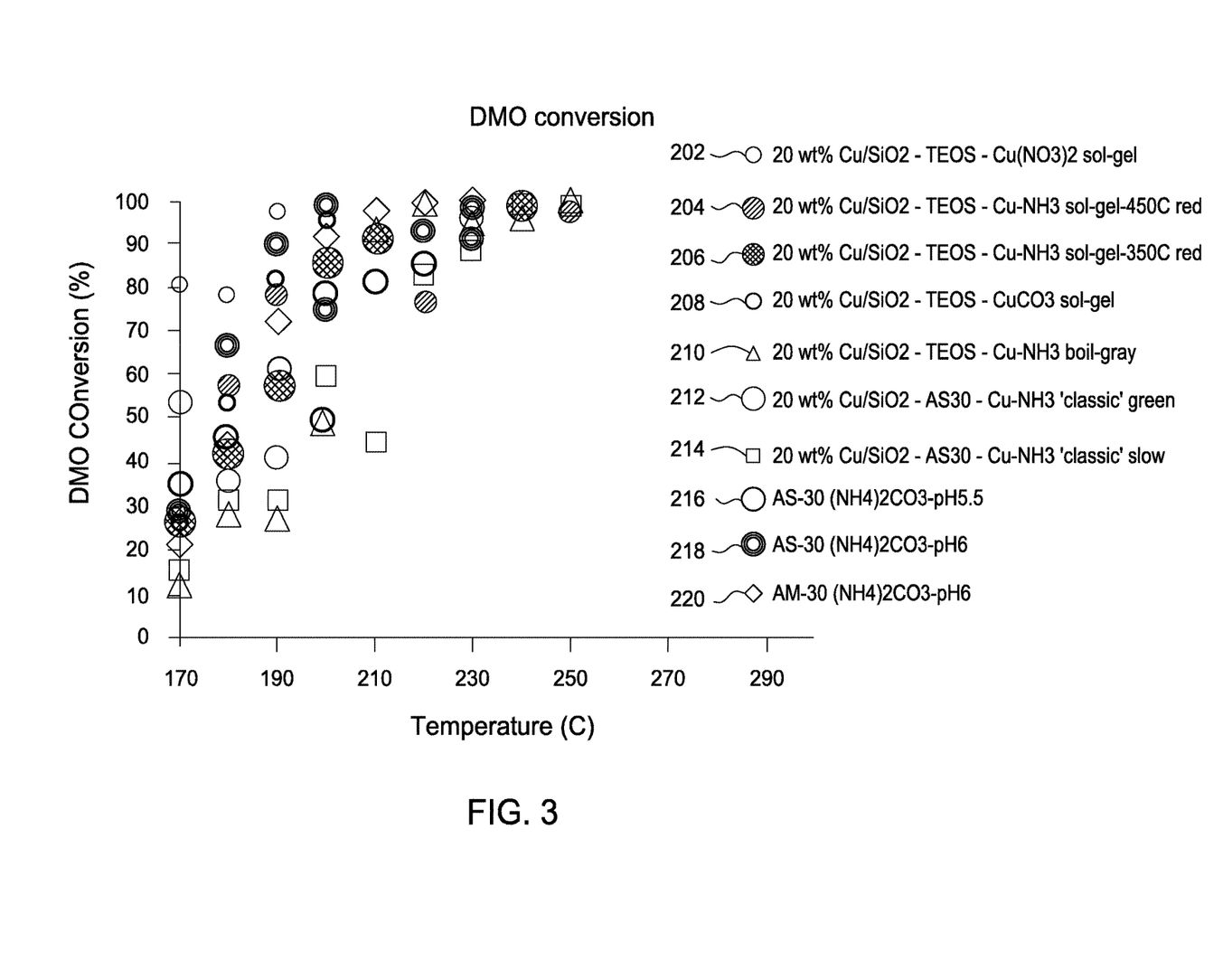
FIG. 3 illustrates the conversion of DMO to EG and MG, under the same hydrogenation conditions as FIG. 2, according to an embodiment.

FIG. 3 illustrates the conversion of DMO to EG and MG under the same hydrogenation conditions as FIG. 2, according to an embodiment of the present disclosure. As shown in FIG. 3, hydrogenation using a catalyst formed by gelation of $Cu(NO_3)_2$ in TEOS (202) displays the highest conversion, but, as shown in FIG. 2, the lowest selectivity of all catalysts tested. As shown in FIG. 3, hydrogenation reactions performed using catalysts prepared from ammonium carbonate (208, 216, 218 and 220) result in higher conversion % over a broad range of temperatures as compared to the catalysts synthesized by ammonia evaporation or other processes (202-206, 210-214). (Note: 204 data point overlaps with 216 data point at 170° C.; 218 data point overlaps 202 data point at 200° C.; 202 data point overlaps 220 data point at 210° C.; 208, 212, and 218 data points overlap 206 data point at 210° C.; 202, 208, and 216 data points overlap 220 data point at 220° C.; 204 data point overlaps with 210 data point at 240° C.). FIG. 2 and FIG. 3 cumulatively illustrate that preparation of catalysts using an ammonium salt, such as ammonium carbonate, results in hydrogenation catalysts with a superior combination of both selectivity and efficient conversion as compared to combination selectivity and conversion of catalysts not prepared using an ammonium salt. Catalysts synthesized with ammonium salts also show prolonged catalytic activity as compared to catalysts synthesized without an ammonium salt.

The total surface area of catalysts 202-220 may be determined using $N_2$ adsorption technique (for example, on a volumetric system such as AutosorbIQ ASIQC0100-4 Quantachrome Instruments). After reduction and hydrogenation (about 15 hours), the surface area of the catalysts did not noticeably decrease and the surface area was a function of the original structure and type of porosity of the catalysts 202-220. It was also seen that fine porosity area (pores less than 2 nm) was large for zeolites and remained substantially constant after reduction and hydrogenation.

As determined by X-Ray Diffraction (for example, a Rigaku Smartlab XRD machine), catalyst 202 (prepared by gelification of TEOS-Cu(NO$_3$)$_2$) has the smallest CuO particles of the prepared catalysts 202-220. Catalyst 202 showed the highest DMO conversion at low temperatures of catalysts 202-220 but also generated ethanol as a byproduct thus drastically reducing selectivity %. This suggests that particles of catalyst 202 have a size below an optimum dimension for supported material in order to depress the formation of ethanol. Between the catalysts prepared using silica sol (AS30), it is contemplated that the precipitation agent may be a determining factor, as the unreduced catalysts using ammonia evaporation (212 and 214) show slightly larger CuO particles and an increased presence of Cu silicate. Without being bound by theory, it is possible that this silicate is not active for DMO hydrogenation and 350° C. reduction temperature is not high enough to reduce it to metallic $Cu^0$, thus explaining the lower catalytic activity compared to samples prepared using ammonium carbonate. Catalysts synthesized using an ammonium salt give compounds, such as copper compounds, such as Cu/SiO$_2$ particles, having a particle size in the range of about 10-40 nm, and these catalysts promote selectivity as well as conversion.

Temperature Programmed Reduction (TPR) results for the unreduced catalysts (using, for example, an Autosorb IQ ASIQC0100-4 Quantachrome Instruments machine) show mainly one peak assigned to the dispersed CuO to metallic Cu. The result for the catalysts prepared using AS-30 with ammonia evaporation (212 and 214) show a small second peak assigned to the reduction of "bulk" CuO (larger crystalline phases). The catalysts prepared using sol-gel (204, 206, and 208) show the first peak at lower temperature with the TEOS-Cu(NO$_3$)$_2$ catalyst (202) generating the lowest temperature peak among tested materials. Among the catalysts prepared using TEOS as raw material, the catalyst using TEOS and ammonia evaporation (210) had the highest temperature for the maximum reduction phase which is in accordance with the XRD results as having the largest CuO crystals in this group. While the catalyst Cu/SiO$_2$ AS-30 AE (212 and 214) have the second peak it also has a wider lower temperature peak indicating a wider distribution of CuO on silica and the maximum reduction of this low temperature peak at slightly higher temperature, compared with the catalyst using ammonium carbonate precipitation (Cu/SiO$_2$ AS-30 AC) (216 and 218).

A hydrogenation catalyst, such as Cu/SiO$_2$, used for dimethyl (or diethyl) oxalate hydrogenation (to form ethylene glycol and methanol (ethanol respectively)) may be synthesized via the ammonia evaporation or urea hydrolysis of copper nitrate, silica sol or TEOS (tetraethyl orthosilicate). However, these methods are slow in comparison to use of an ammonium salt, such as ammonium carbonate, as a precipitation agent. Ammonia evaporation techniques typically generate the catalyst precipitate in about one day, and TEOS gelification techniques generate the catalyst precipitate in about 48 hours. Faster methods to achieve catalyst formation, such as Cu/SiO$_2$ formation, may be realized by using ammonium salts, such as ammonium carbonate, with silica sources such as silica sol or TEOS. Furthermore, the details of catalyst synthesis for both ammonia evaporation and urea decomposition techniques can have a large influence in the activity of the catalyst due to variations in particle dimension, crystal dimension, dispersion on a support, etc. Furthermore, besides the variation in copper deposition as a function of the rate of pH change and temperature during boiling associated with slow catalyst deposition, the ammonia evaporation method is likely to lead to hazards (explosions, intoxications, environmental damage) upon scale up.

Apparatus and methods described herein allow improved control of the supported copper particle dimension. Hydrogenation catalyst synthesis using an ammonium salt provides an easily repeatable method generating stable results for this class of catalysts. Apparatus and methods described herein are more precise, efficient, and environmentally favorable compared to ammonia evaporation and urea-based apparatus and methods. Apparatus and methods described herein provide a favorable environmental impact that avoids generating ammonia fumes and free ammonia. Methods of catalyst synthesis described herein allow improved activity of the catalyst due to variations in particle dimension, crystal dimension, dispersion on a support, etc. The variability may be tied to the pH, and the apparatus and methods of catalyst synthesis described herein greatly simplify the process. Furthermore, TEOS and copper nitrate, gelification may require 48 h for gelification itself and ammonia evaporation and urea hydrolysis for silica sol and copper nitrate generally require one day, while the same process is achieved in less than a minute using fast ammonia gelification or ammonium carbonate precipitation for TEOS and copper carbonate and comparable time for the precipitation of aqueous silica sol and copper nitrate mixture. Apparatus and methods of the present disclosure achieve good quality catalyst much faster than apparatus and methods known in the art. Apparatus and methods of the present disclosure allow for efficient commercial-scale production of ethylene glycol.

While the foregoing is directed to embodiments of the present disclosure, other and further embodiments of the present disclosure may be devised without departing from the basic scope thereof.

The invention claimed is:

1. A method of hydrogenating an oxalate, comprising:
preparing a hydrogenation catalyst having a particle size between about 10 nm and about 40 nm by a deposition-precipitation of a mixture consisting of water, Cu(NO$_3$)$_2$, an ammonium salt, and a zeolite comprising a mol ratio of SiO$_2$:Al$_2$O$_3$ of between 0.1:100 and 100:0.1;
flowing the hydrogenation catalyst to a reactor;
flowing a hydrogen source to the reactor;
flowing an oxalate material to the reactor, wherein the hydrogenation catalyst, the hydrogen source, and the oxalate material comprise a reaction mixture; and
reacting the oxalate material to form ethylene glycol.

2. The method of claim 1, further comprising pressurizing the reactor to between about 100 PSI to about 500 PSI.

3. The method of claim 1, further comprising maintaining a temperature inside the reactor between about 150° C. to about 240° C.

4. The method of claim 1, wherein the reaction mixture comprises the hydrogen source between about 50 volume % to about 99.9 volume %.

5. The method of claim 1, further comprising flowing a carrier gas to the reactor, wherein the reaction mixture comprises between about 1 volume % to about 15 volume % of the carrier gas.

6. The method of claim 1, wherein a mol ratio of hydrogen source to oxalate in the reaction mixture is between about 90:1 to about 50:1.

7. The method of claim 1, wherein a weight hourly space velocity (WHSV) is between about 0.3 and about 10.

8. The method of claim 1, wherein the hydrogen source reduces the hydrogenation catalyst before flowing the oxalate to the reactor.

9. The method of claim 8, wherein a temperature inside the reactor during the reduction is between about 300° C. to about 400° C. for about 2 hours to about 6 hours.

10. The method of claim 9, wherein the temperature inside the reactor is reduced before the flowing the oxalate to the reactor.

11. The method of claim 1, wherein the mixture consisting of water, $Cu(NO_3)_2$, an ammonium salt, and a zeolite comprising a mol ratio of $SiO_2:Al_2O_3$ of between 0.1:100 and 100:0.1 forms a catalyst precipitate.

12. The method of claim 11, further comprising:
calcining the precipitate between about 300° C. to about 500° C. for between about 2 hours to about 24 hours.

13. The method of claim 1, wherein the ammonium salt is ammonium carbonate $((NH_4)_2CO_3)$, ammonium acetate $((NH_4)OCOCH_3)$, ammonium chloride $(NH_4Cl)$, ammonium bicarbonate $((NH_4)OCOOH)$, or mixtures thereof.

14. The method of claim 1, wherein the ammonium salt is ammonium carbonate $((NH_4)_2CO_3)$.

15. The method of claim 1, wherein the ammonium salt is ammonium acetate $((NH_4)OCOCH_3)$.

16. The method of claim 1, wherein the ammonium salt is ammonium chloride $(NH_4Cl)$.

17. The method of claim 1, wherein the ammonium salt is ammonium bicarbonate $((NH_4)OCOOH)$.

18. The method of claim 1, wherein the zeolite comprises a mol ratio of $SiO_2:Al_2O_3$ of between about 50:1 and about 100:0.1.

19. The method of claim 1, wherein the zeolite comprises a mol ratio of $SiO_2:Al_2O_3$ of about 80:1.

* * * * *